US009792255B2

(12) United States Patent
Kusakabe et al.

(10) Patent No.: US 9,792,255 B2
(45) Date of Patent: Oct. 17, 2017

(54) ELECTRONIC STATE CALCULATION METHOD, ELECTRONIC STATE CALCULATION DEVICE, AND RECORDING MEDIUM

(75) Inventors: Koichi Kusakabe, Osaka (JP); Isao Maruyama, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 1063 days.

(21) Appl. No.: 13/817,586

(22) PCT Filed: Aug. 17, 2011

(86) PCT No.: PCT/JP2011/068589
§ 371 (c)(1),
(2), (4) Date: Feb. 19, 2013

(87) PCT Pub. No.: WO2012/023563
PCT Pub. Date: Feb. 23, 2012

(65) Prior Publication Data
US 2013/0151174 A1    Jun. 13, 2013

(30) Foreign Application Priority Data

Aug. 18, 2010 (JP) .................................. 2010-183375

(51) Int. Cl.
*G06F 17/11* (2006.01)
*G01N 27/00* (2006.01)
(Continued)

(52) U.S. Cl.
CPC ............ *G06F 17/11* (2013.01); *G06F 19/701* (2013.01); *G01N 23/2251* (2013.01);
(Continued)

(58) Field of Classification Search
CPC ........ G06F 17/11; G06F 19/00; G06F 19/701; G06F 19/16; G06F 19/704;
(Continued)

(56) References Cited

U.S. PATENT DOCUMENTS 5,335,238 A * 8/1994 Bahns ....................... H01J 7/00
315/111.41
5,345,465 A * 9/1994 Bahns ....................... H01J 7/00
315/111.21
(Continued)

FOREIGN PATENT DOCUMENTS

JP    2006-277582 A    10/2006
JP    2008-021259       1/2008
(Continued)

OTHER PUBLICATIONS

Arjan Berger, Current-Density Functionals, NPL, 2006.*
(Continued)

*Primary Examiner* — Carol S Tsai
(74) *Attorney, Agent, or Firm* — Renner Otto Boisselle & Sklar, LLP (57) ABSTRACT

A method of calculating an electronic state of a material by using a calculation device, wherein the calculation device sets a set containing, as elements, a plurality of operation models, where each of operation models provides an approximate solution to the electronic state of the material, determines an optimized operation model that are close in distance in a space formed by the set while defining a direction in which the calculated self-consistent solutions of the effective Hamiltonian of an electron system continuously change, evaluates a variational energy of the electron system by the self-consistent solution, updates the operation model so that the evaluated variational energy approaches an energy of an exact solution to be calculated and further, so that the variational energy forms a monotonically decreasing convex function, and calculates the exact solution of the electronic state from one or a plurality of variational energy series.

9 Claims, 6 Drawing Sheets

(51) Int. Cl.
*G06F 19/00* (2011.01)
*G01N 23/225* (2006.01)

(52) U.S. Cl.
CPC ...... *G01N 27/00* (2013.01); *H01J 2237/2445* (2013.01); *H01J 2237/24485* (2013.01); *H01J 2237/2516* (2013.01)

(58) Field of Classification Search
CPC .............. G01N 23/2251; G01N 27/00; H01J 2237/2516; H01J 2237/2445; H01J 2237/25585
USPC ............ 702/57; 703/2; 372/37, 76; 250/207, 250/372, 458.1; 315/111.21, 111.41
See application file for complete search history.

(56) References Cited

U.S. PATENT DOCUMENTS

| | | | | |
|---|---|---|---|---|
| 5,554,844 | A | * | 9/1996 | Namatame ......... G01N 23/2251 250/207 |
| 7,904,283 | B2 | | 3/2011 | Merz, Jr. ................. G06F 19/16 702/19 |
| 8,082,131 | B2 | * | 12/2011 | Kusakabe ............. G06F 19/701 703/13 |
| 8,386,193 | B2 | * | 2/2013 | Aoki ..................... G06F 19/701 702/27 |
| 9,262,591 | B2 | * | 2/2016 | Kusakabe ............. G06F 19/701 |
| 2003/0013607 | A1 | * | 1/2003 | Morikawa ................ B01J 21/06 502/200 |
| 2005/0027458 | A1 | * | 2/2005 | Merz ....................... G06F 19/16 702/19 |
| 2007/0290966 | A1 | * | 12/2007 | Lee .................. G02F 1/133606 345/87 |
| 2008/0050549 | A1 | * | 2/2008 | Lackey .................. B44C 5/005 428/66.6 |
| 2009/0093973 | A1 | * | 4/2009 | Kusakabe ............. G06F 19/701 702/27 |
| 2011/0191077 | A1 | * | 8/2011 | Kusakabe ............. G06F 19/701 703/2 |
| 2011/0313741 | A1 | * | 12/2011 | Langhoff ............. G06F 19/704 703/2 |

FOREIGN PATENT DOCUMENTS

| | | |
|---|---|---|
| JP | 2008-052308 | 3/2008 |
| JP | 2010-165924 | 7/2010 |
| WO | 2007/141942 A1 | 12/2007 |
| WO | 2010/023943 A1 | 3/2010 |

OTHER PUBLICATIONS

International Search Report for corresponding International Application No. PCT/JP2011/068589 mailed Sep. 20, 2011.
Kasai et al., "Introduction to Computational Materials Design", Osaka University Press, Oct. 20, 2005.
"Meeting Abstracts of the Physical Society of Japan", vol. 65, Issue 1 (65$^{th}$ Annual Meeting ), Pt. 2, p. 283, Mar. 1, 2010.
K. Kusakabe, "Pair-Hopping Mechanism for Layered Superconductors", Journal of the Physical Society of Japan, vol. 78, No. 11, Nov. 10, 2009, 114716.
K. Kusakabe et al., "A self-consistent first-principles calculation scheme for correlated electron systems", Phys.: Condens. Matter 19 (Oct. 18, 2007) 445009.
Masanori Koyama, "The Nano-Simulation Handbook", 1$^{st}$ Edition, Kyoritsu Shuppan Co., Ltd., Jul. 15, 2006, pp. 148 to 153, 172 to 173, 180 to 181, 200 to 201.
K. Kusakabe, "Determination of the Mott insulating transition by the multi-reference density functional theory", J. Phys.: Condens. Matter 19, 365229-1-4 (2007).
Kusakabe et al., "A microscopic mechanism of Coulomb driven effective negative interaction for the high-temperature superconductivity", J. Phys. Soc. Jpn. 77, Suppl. C, pp. 109-112 (2008).

* cited by examiner

ELECTRONIC STATE CALCULATION METHOD, ELECTRONIC STATE CALCULATION DEVICE, AND RECORDING MEDIUM

CROSS-REFERENCE TO RELATED APPLICATIONS

This application is the national phase under 35 U.S.C. §371 of PCT International Application No. PCT/JP2011/68589 which has an International filing date of Aug. 17, 2011 and designated the United States of America.

BACKGROUND

1. Technical Field

The present application relates to an electronic state calculation method, an electronic state calculation device and a recording medium for obtaining an electronic state of a material by a calculation.

2. Description of the Related Art

Conventionally, there exits a calculation theory called a first-principle calculation theory of estimating physical or chemical properties of a material (hereinafter, referred to as properties) according to a basic rule of quantum mechanics. Of this calculation theory, a calculation theory based on a density functional theory is present in which properties such as mechanical properties including elasticity, conductive properties including superconductive properties, a dielectric property, and a magnetic property are approximately reproduced and the calculation scale is within an implementable range. This calculation theory has already been applied to material design, and there exist a multiplicity of examples with its expectation accuracy and accuracy limit verified through experiments.

Although the calculation theory based on the density functional theory includes a self-consistent calculation theory by local density approximation (LDA), it is known that the calculation result does not always show the same properties as in experiments.

As calculation techniques based on the density functional theory, a plurality of approximate calculation techniques are known such as generalized-gradient approximation (GGA), GW approximation, GW+Γ approximation and LDA+U approximation positioned as techniques to overcome a problem with the LDA, and regarding these approximate calculation techniques, it is also known that the calculation result does not always show the same properties as in experiments.

The above-mentioned approximate calculation techniques all have a problem that they do not provide a method for always attaining the properties shown by a real solution (exact solution) by a finite number of times of calculation. That is, no self-consistent calculation theory is present that always ensures reproduction of the properties of the real solution while utilizing a high-accuracy one-electron basis provided by the LDA.

On the other hand, one of the inventors of the present application has proposed a fluctuation reference determination method as an effective many-electron calculation based on a multi-reference density functional method. By this method, the reproduction accuracy of the physical quantities can be improved with a given accuracy by providing an extended Kohn-Sham equation to reproduce a fluctuation variable (correlation function) having a positive definite property such as local density fluctuations in addition to the one-electron density. According to this calculation technique, the total energy, the one-electron density and the specified fluctuation variable of a material are simultaneously reproduced through the determination of the minimum energy state of a Hamiltonian. Further, by using, as the initial values, a model determined by the extended Kohn-Sham equation and its stability solution, a time development equation to reproduce the total energy, the one-electron density and the canonical correlation function is provided, and a high-accuracy first-principle electron state calculation method for reproducing external field responses (such as responses to dynamic deformation and electric field application) of the material is provided.

However, the effective many-electron calculation based on the multi-reference density functional method is a calculation technique for which a reference calculation such as a quantum Monte Carlo method, a transcorrelated method, a configuration interaction method, a perturbational calculation/Green's function method or an effective potential method is inevitable. For this reason, the reproduction accuracy of the physical quantities depends on the calculation accuracy of the reference calculation, and a calculation technique by which the real solution is attained beyond the calculation accuracy of the reference calculation is not provided.

Accordingly, one of the inventors of the present application has further proposed an electronic state calculation method, an electronic state calculation device, a computer program and a recording medium by which exact solution evaluation can be performed by providing a quantum-mechanical variation calculation theory using a density functional (density functional variational method) and a method that provides an approximation model sequence attaining the exact solution in a model space as a Banach space containing the exact solution, and obtaining a stable numerical solution within a range permitted by the calculator resources.

However, when the goal is limited to reproduction of only the physical or chemical properties of a material, the method that attains the exact solution by an approximation model sequence attaining the exact solution in the model space does not use the attainment of the properties of the exact solution by a smaller finite number of times of calculation.

SUMMARY

The present application is made in view of such circumstances, and an object thereof is to provide an electronic state calculation method, an electronic state calculation device and a recording medium which store a computer program capable of attaining the properties shown by the exact solution by a finite number of calculation procedures while searching for a plurality of calculation paths, according to the variation principle of the density functional variational method provided in a model space by using, as the starting point, an existing approximation model such as the local density approximation method, the generalized-gradient approximation method, a Hartree-Fock method, the configuration interaction method or a perturbation MP (Moeller-Pleasset) method.

An electronic state calculation method of the present application, where the method of calculating an electronic state of a material by using a calculation device, is characterized in that the calculation device sets a set containing, as elements, a plurality of operation models, where each of operation models provides an approximate solution to the electronic state of the material, determines, in order to specify all operation models, for each operation model, an effective Hamiltonian including effective interactions that act on an electron system containing two or more electrons existing on a plurality of electron orbitals, determines, in a process of calculating a self-consistent solution of the effective Hamiltonian by using each of the operation models in the set, an optimized operation model among a plurality of operation models that are close in distance in a space formed by the set, based on a quantum mechanical variational method while defining a direction in which the calculated self-consistent solutions continuously change, evaluates, when the optimized operation model is successively updated, a variational energy of the electron system by the self-consistent solution of the effective Hamiltonian, updates the operation model so that the evaluated variational energy approaches an energy of an exact solution to be calculated and further, so that the variational energy forms a monotonically decreasing convex function, and calculates the exact solution of the electronic state from one or a plurality of variational energy series.

The electronic state calculation method of the present application is characterized in that the effective Hamiltonian is determined through a procedure of determining non-local operators indicating fluctuations as the effective interactions, based on a local density approximation method, a generalized-gradient approximation method or a Hartree-Fock method.

The electronic state calculation method of the present application is characterized in that the fluctuations include density fluctuations which are equal to the deviation of a Hartree mean-field term and a Coulomb interaction.

The electronic state calculation method of the present application is characterized in that among one or a plurality of series of the operation models that provide a series of the variational energy that approaches the exact solution, one is determined that includes an operation model where a quantum phase shown by the electronic state does not make a transition to the other, the quantum phase equated with the exact solution is provided and the self-consistent solution of the effective Hamiltonian is attained by a minimum number of calculation steps.

The electronic state calculation method of the present application is characterized in that the self-consistent solution by each of the operation models is obtained by a parallel calculation using an LAPW (linearized augmented plane wave) method, a PAW (projector augmented wave) method or a numerical basis expansion method.

An electronic state calculation device of the present application, where the device calculates an electronic state of a material, is characterized by comprising means for setting a set containing, as elements, a plurality of operation models, where each of operation models provides an approximate solution to the electronic state of the material, means for determining, in order to specify all operation models, for each operation model, an effective Hamiltonian including effective interactions that act on an electron system containing two or more electrons existing on a plurality of electron orbitals, means for determining, in a process of calculating a self-consistent solution of the effective Hamiltonian by using each of the operation models in the set, an optimized operation model among a plurality of operation models that are close in distance in a space formed by the set, based on a quantum mechanical variational method while defining a direction in which the calculated self-consistent solutions continuously change, means for evaluating, when the optimized operation model is successively updated, a variational energy of the electron system by the self-consistent solution of the effective Hamiltonian, means for updating the operation model so that the evaluated variational energy approaches an energy of an exact solution to be calculated and further, so that the variational energy forms a monotonically decreasing convex function, and means for calculating the exact solution of the electronic state from one or a plurality of variational energy series.

The electronic state calculation device of the present application is characterized in that the effective Hamiltonian is determined through a procedure of determining non-local operators indicating fluctuations as the effective interactions, based on a local density approximation method, a generalized-gradient approximation method or a Hartree-Fock method.

The electronic state calculation device of the present application is characterized in that the fluctuations include density fluctuations which are equal to the deviation of a Hartree mean-field term and a Coulomb interaction.

The electronic state calculation device of the present application is characterized in that among one or a plurality of series of the operation models that provide a series of the variational energy that approaches the exact solution, one is determined that includes an operation model where a quantum phase shown by the electronic state does not make a transition to the other, the quantum phase equated with the exact solution is provided and the self-consistent solution of the effective Hamiltonian is attained by a minimum number of calculation steps.

The electronic state calculation device of the present application is characterized in that the self-consistent solution by each of the operation models is obtained by a parallel calculation using an LAPW (linearized augmented plane wave) method, a PAW (projector augmented wave) method or a numerical basis expansion method.

A recording medium which stores a computer program that causes a computer to calculate an electronic state of a material, is characterized in that the computer program causing the computer to execute a step of setting a set containing, as elements, a plurality of operation models, where each of operation models provides an approximate solution to the electronic state of the material, a step of determining, in order to specify all operation models, for each operation model, an effective Hamiltonian including effective interactions that act on an electron system containing two or more electrons existing on a plurality of electron orbitals, a step of determining, in a process of calculating a self-consistent solution of the effective Hamiltonian by using each of the operation models in the set, an optimized operation model among a plurality of operation models that are close in distance in a space formed by the set, based on a quantum mechanical variational method while defining a direction in which the calculated self-consistent solutions continuously change, a step of evaluating, when the optimized operation model is successively updated, a variational energy of the electron system by the self-consistent solution of the effective Hamiltonian, a step of updating the operation model so that the evaluated variational energy approaches an energy of an exact solution to be calculated and further, so that the variational energy forms a monotonically decreasing convex function, and a step of calculating the exact solution of the electronic state from one or a plurality of variational energy series.

According to the present application, in a method, a device and a computer program that calculate an electronic state of a material by using a calculation device, a finite number of calculation procedures of reproducing the properties shown by the electronic state of the material are provided based on the multi-reference density functional theory.

According to the present application, the calculation device automatically determines the properties of the electronic state shown by the exact solution of the material, through the determination of the self-consistent solution of a determination equation provided by an operation model by the multi-reference density functional theory.

According to the present application, it is ensured by the principle of the density functional theory that fluctuation variables (correlation functions) or multiple order parameters having a positive definite property such as local density fluctuations necessary for reproducing the properties shown by the exact solution are countable and finite.

In a case of the present application, the operation model used in the calculation process is determined so that the model-to-model distance decreases in the process of obtaining the self-consistent solution of the effective Hamiltonian showing the effective interactions that act between electrons by using, as the starting point, the operation model that provides an approximate solution to the electronic state of the material. Thereby, an optimization procedure of a new operator space is provided, and by generating a series of higher-ranked models which series cannot be formed by a down folding method based on the renormalization idea, a method of evaluation of the properties provided by the exact solution can be provided by a finite number of calculation procedures.

In a case of the present application, since a plurality of paths that can attain the exact solution can be provided in a model space containing a wide variety of operation models, the path to incorporate the electron correlation can be set as appropriate. For example, by successively incorporating a strong correlation effect from the Fermi level and considering all the correlations dependent on an energy scale or a space scale, an operator asymptotic to the Coulomb interaction can be incorporated.

In a case of the present application, since the operation to obtain the self-consistent solution can be executed in parallel, the calculation speed is improved by implementing a parallel calculation. Moreover, the calculation speed is improved by using a parallelization calculation method implemented by an existing first-principle calculation method including the density functional method at each step of the calculation.

In a case of the present application, a technique can be provided that attains the properties shown by the exact solution by a finite number of calculation steps by using, as the starting point, an existing operation model including the local density approximation method, the generalized-gradient approximation method, the Hartree-Fock method, the configuration interaction method or the perturbation MP method.

In a case of the present application, a technique is provided in which the expression of the effective Hamiltonian includes, as operators, effective interactions asymptotic to the Coulomb interaction between electrons in the neighborhood of the Fermi level.

In a case of the present application, a technique is provided of obtaining the self-consistent solution by each operation model by using an expression method of a high-accuracy one-electron wave function having undergone basis expansion, by using a method such as an LAPW method (linearized augmented plane wave method), a PAW (projector augmented wave) method or a numerical basis expansion method.

In a case of the present application, by using a model system and its stability solution as the initial values, a time development equation to reproduce the total energy, the one-electron density and the canonical correlation is further provided, and a high-accuracy first-principle electronic state calculation method of reproducing external field responses (such as responses to dynamic deformation and electric field application) of the material can be provided.

In a case of the present application, the calculation procedure capable of efficiently attaining the properties shown by the exact solution can be determined within a range using the provided calculation resources.

Consequently, in a new quantum design technique by which material design is performed by using a quantum simulator by a calculator simulation, material design by a calculation device is made possible such as the provision of a quantum device formation element design method such as spin electronics and molecular electronics, the provision of an energy problem avoidance method by electronic application, the provision of an environment problem and resources and energy problem avoidance type material solution by low environmental loads or strategic element selection, design of a new sensor, design of a biocompatible material, and design of a medicine.

The above and further objects and features of the invention will more fully be apparent from the following detailed description with accompanying drawings.

DETAILED DESCRIPTION

Hereinafter, the present application will be concretely described based on the drawings showing embodiments thereof.

First Embodiment

The calculation principle of an electronic state calculation method according to the present embodiment is as follows:
In the present embodiment, as a method of determining an optimized operation model that realizes the properties shown by the exact solution of the electronic state, it is aimed to reproduce the properties through numerically obtaining an order parameter which is the electron density generated by a Coulomb many-body system in the ground state. The electron density is a physical quantity that can be observed by an experiment, and its existence is known. An energy $E_0$ of the ground state of the Coulomb many-body system can be numerically evaluated since it satisfies the following expression:

$$E_0 \leq \min_i \left\{ \min_\Psi \overline{G}_{X_i, \varepsilon_i, g_i}[\Psi] + \Delta \overline{E}_{X_i, \varepsilon_i, g_i}[\Psi_{X_i, \varepsilon_i, g_i}] \right\}. \quad \text{(Formula 1)}$$

The energy functional $\bar{G}_{X_i, \in_i, g_i}$ is defined by the following formula:

$$\bar{G}_{X_i, \in_i, g_i}[\Psi] = \langle \Psi | \hat{T} + \hat{V}_{red}^{X_i} | \Psi \rangle + \frac{e^2}{2} \int dr dr' \frac{n_\Psi(r) n_\Psi(r')}{|r - r'|} + \quad \text{(Formula 2)}$$
$$E_{\epsilon_i}^{local}[\Psi] + E_{g_i}^{non-local}[\Psi] + \int dr v_{ext}(r) n_\Psi(r).$$

Moreover, $\Delta \bar{E}_{X_i, \in_i, g_i}$ is defined by the following formula:

$$\Delta \bar{E}_{X_i, \in_i, g_i}[\Psi] = \quad \text{(Formula 3)}$$
$$\frac{e^2}{2} \int dr dr' \frac{1}{|r - r'|} \langle \Psi | : (\hat{n}(r) - \langle \hat{n}(r) \rangle)(\hat{n}(r') - \langle \hat{n}(r') \rangle) : | \Psi \rangle -$$
$$E_{\epsilon_i}^{local}[\Psi] - E_{g_i}^{non-local}[\Psi] - \langle \Psi | \hat{V}_{red}^{X_i} | \Psi \rangle.$$

Here, $\bar{G}_{X_i, \in_i, g_i}$ is the energy functional with respect to a wave function $\Psi$ of an electron system expressed by an operation model, and $\Delta \bar{E}_{X_i, \in_i, g_i}$ is an energy functional to correct the difference of the energy caused when the variational energy of a Coulomb system is evaluated.

Here, $\Psi$ is a many-particle wave function, T is an operator giving the kinetic energy, $V_{red}^{X_i}$ is an operator expressed by the following formula 4. While the operator T and the operator $V_{red}^{X_i}$ are expressed by hatted letters in the formulae, they are not hatted in the specification. In formula 2, e is the electric charge of the electron, $n_\Psi(r)$ is the electron density provided by $\Psi$ at a position vector r, and $v_{ext}(r)$ is an external scalar potential.

$$\langle \Psi | \hat{V}_{red}^{X_i} | \Psi \rangle = \quad \text{(Formula 4)}$$
$$\sum_n \langle P^{(i)} \left[ \Xi_n^{(i)} \begin{pmatrix} (\hat{Y}_n^{(i)} - \langle \hat{Y}_n^{(i)} \rangle)^\dagger, \hat{Y}_n^{(i)} - \langle \hat{Y}_n^{(i)} \rangle, \\ (\hat{Z}_n^{(i)} - \langle \hat{Z}_n^{(i)} \rangle)^\dagger, \hat{Z}_n^{(i)} - \langle \hat{Z}_n^{(i)} \rangle \end{pmatrix} \right]_{\alpha_n^{(i)}} P^{(i)} \rangle,$$

$$X_i = (\Xi_n^{(i)}, \hat{Y}_n^{(i)}, \hat{Z}_n^{(i)}, \alpha_n^{(i)}),$$

$$\left[ \Xi_n^{(i)} \begin{pmatrix} (\hat{Y}_n^{(i)} - \langle \hat{Y}_n^{(i)} \rangle)^\dagger, \hat{Y}_n^{(i)} - \langle \hat{Y}_n^{(i)} \rangle, \\ (\hat{Z}_n^{(i)} - \langle \hat{Z}_n^{(i)} \rangle)^\dagger, \hat{Z}_n^{(i)} - \langle \hat{Z}_n^{(i)} \rangle \end{pmatrix} \right]_\alpha \equiv (1 - \alpha) :$$

$$\Xi_n^{(i)} \begin{pmatrix} (\hat{Y}_n^{(i)} - \langle \hat{Y}_n^{(i)} \rangle)^\dagger, \hat{Y}_n^{(i)} - \langle \hat{Y}_n^{(i)} \rangle, \\ (\hat{Z}_n^{(i)} - \langle \hat{Z}_n^{(i)} \rangle)^\dagger, \hat{Z}_n^{(i)} - \langle \hat{Z}_n^{(i)} \rangle \end{pmatrix} :$$

$$+ \alpha \Xi_n^{(i)} \begin{pmatrix} (\hat{Y}_n^{(i)} - \langle \hat{Y}_n^{(i)} \rangle)^\dagger, \hat{Y}_n^{(i)} - \langle \hat{Y}_n^{(i)} \rangle, \\ (\hat{Z}_n^{(i)} - \langle \hat{Z}_n^{(i)} \rangle)^\dagger, \hat{Z}_n^{(i)} - \langle \hat{Z}_n^{(i)} \rangle \end{pmatrix},$$

$$\hat{Y}_n^{(i)} = \sum_{l_1, l_2, \sigma} c_{l_1 \sigma}^{(i)\dagger} f_{n,+,l_1,l_2,\sigma} c_{l_2 \sigma}^{(i)},$$

$$\hat{Z}_n^{(i)} = \sum_{l_1, l_2, \sigma} c_{l_1 \sigma}^{(i)\dagger} f_{n,-,l_1,l_2,\sigma} c_{l_2 \sigma}^{(i)}.$$

Here, $X_i$ is a set consisting of a pair of a parameter that determines the model and an operator. $P^{(i)}$ is a projection operator. Moreover, the symbol ::, which is called a normal order, specifies order of operators so that creation operators appear before annihilation operators by permutating the operators according to an exchange rule of fermion operators. Moreover, $Y_n^{(i)}$ and $Z_n^{(i)}$ are operators provided by annihilation operators, $c_{l_0}^{(i)}$, where each of $c_{l_0}^{(i)}$ is given for an electron on an orbital l provided by a complete set of one body wave functions, and $f_{n, +, l, \sigma}$, $f_{n, -, l, \sigma}$ are complex constants. $\alpha_n^{(i)}$ is a parameter to control a self-interaction correction. $\Xi_n^{(i)}$ is a function with respect to the operators $Y_n^{(i)}$ and $Z_n^{(i)}$, and may be, particularly, a polynomial function, although it is desirable that the expectation value thereof be known to have a finite lower bound.

Moreover, $E_{\in_i}^{local}[\Psi]$ and $E_{g_i}^{non-local}[\Psi]$ in formula 2 are a model energy functional having locality and a model energy functional having non-locality; for example, functionals defined as follows may be used:

$$E_{\epsilon_i}^{local}[\Psi] = \int \epsilon_i(n_\Psi(r)) n_\Psi(r) dr, \quad \text{(Formula 5)}$$

$$E_{g_i}^{non-local}[\Psi] = \sum_{l_1, l_2, \sigma} g_i(l_1, l_2, \sigma) \langle \Psi | c_{l_1 \sigma}^{(i)\dagger} c_{l_2 \sigma}^{(i)} | \Psi \rangle.$$

Here, $\in_i(n)$ is a bounded monotonically decreasing continuous function and $g_i(l_1, l_2, \sigma)$ is a real-valued coefficient; these are provided at the time of input. Although these may be re-optimized by using the solution of the Kohn-Sham equation determined in the middle of the calculation process, the result is unaffected irrespective of $\in_i$ and/or $g_i$ when the quantum fluctuations incorporated through formula 4 are qualitatively and quantitatively enough, because of securement of a sufficient calculation scale.

The introduction of a model by the effective interactions of formulae 2, 3, 4 and 5 is one feature of the present application. By optimizing the function $\Xi_n^{(i)}$ with respect to the operators, the bounded monotonically decreasing continuous function $\in_i(n)$ and $g_i(l_1, l_2, \sigma)$, an optimization model series that enables a high-efficiency, high-speed and high-accuracy calculation within the range of the calculation resources can be searched for.

For formula 4, by introducing effective many-particle interactions which are separated into channels based on the density fluctuations of the Coulomb system, the following formula may be used as a concrete expression:

$$\langle \Psi | \hat{V}_{red}^{X_i} | \Psi \rangle = \quad \text{(Formula 6)}$$

$$\sum_n X_n^{(i)} \langle P^{(i)} \left\{ \begin{array}{l} [(\hat{Y}_n^{(i)} - \langle \hat{Y}_n^{(i)} \rangle)^\dagger (\hat{Y}_n^{(i)} - \langle \hat{Y}_n^{(i)} \rangle)]_{\alpha_n^{(i)}} - \\ [(\hat{Z}_n^{(i)} - \langle \hat{Z}_n^{(i)} \rangle)^\dagger (\hat{Z}_n^{(i)} - \langle \hat{Z}_n^{(i)} \rangle)]_{\alpha_n^{(i)}} \end{array} \right\} P^{(i)} \rangle,$$

$$X_i = (X_n^{(i)}, \hat{Y}_n^{(i)}, \hat{Z}_n^{(i)}, \alpha_n^{(i)}),$$

$$[Y^\dagger Y]_\alpha = (1 - \alpha) : Y^\dagger Y : + \alpha Y^\dagger Y.$$

Formula 1 provides a variational principle that holds in the model space. When one set a limit to a special case of $E_{g_i}^{non-local}[\Psi]$, the proof of this principle is open to the public (for example, see K. Kusakabe, J. Phys. Soc. Jpn 78, 114716 (2009)). For this reason, an evaluation formula similar to formula 1 is provided as an inequality. Although the presence of a condition for satisfying the equal sign is shown, no strict equal sign is achieved by a calculation with finite calculator resources. However, through obtaining a numerical sequence of evaluated values of the variational energy, the energy $E_0$ in the ground state can be numerically evaluated by integrating sufficient calculation results (see Patent Document 2). The present application uses the fact that this variation principle holds with respect to a wide range of energy functionals. Further, by preparing this calculation process more than one in number, a finite number of times of calculation process to derive the physical properties shown by the exact solution is provided more than one in number, whereby a high-efficiency, high-speed and high-accuracy calculation method can be found within the range of the calculation resources.

The principle that provides formula 1 is strictly shown as follows. Using an expression that provides Coulomb fluctuations without separating the self-interaction correction term, a residual exchange correlation energy functional $\Delta E_{Xi, \in i, gi}[\Psi]$ is introduced by the following formula:

$$\Delta E_{X_i,\varepsilon_i,g_i}[\Psi] = \frac{e^2}{2}\int d\lambda \int dr dr' \frac{1}{|r-r'|}$$
$$\langle \Psi^\lambda_{n_\Psi}| : (\hat{n}(r) - n_\Psi(r))(\hat{n}(r') - n_\Psi(r')) : |\Psi^\lambda_{n_\Psi}\rangle -$$
$$E^{local}_{\varepsilon_i}[\Psi] - E^{non-local}_{g_i}[\Psi] + \min_{\Psi' \to n_\Psi} \langle \Psi'|\hat{T}|\Psi'\rangle -$$
$$\min_{\Psi' \to n_\Psi} \langle \Psi'|\hat{T} + \hat{V}^{X_i}_{red}|\Psi'\rangle.$$

(Formula 7)

Here, the integral with respect to λ is a quantity defined based on a Lebesgue integral with respect to a λ-differential of the energy functional (see formula 8) by a constrained search method obtained by multiplying the Coulomb interaction by λ, and the correction at points where a finite number of jumps of the λ Dini derivative of $F_\lambda[\Psi]$ are caused, and the existence thereof is shown. Within a range where the density is not changed, a phase transition by the remaining correlation is caused at the point where a jump of the λ Dini derivative happens.

$$F_\lambda[\Psi] = \min_{\Psi' \to n_\Psi} \langle \Psi'|\hat{T} + \lambda \hat{V}_{ee}|\Psi'\rangle.$$

(Formula 8)

At this time, by replacing $\Delta E bar_{Xi, \in i, gi}[\Psi]$ of formula 1 with $\Delta E_{Xi, \in i, gi}[\Psi]$ defined by formula 7, the following expression can be obtained:

$$E_0 \le \min_i \left\{ \min_\Psi \bar{G}_{X_i,\varepsilon_i,g_i}[\Psi] + \Delta E_{X_i,\varepsilon_i,g_i}[\Psi_{X_i,\varepsilon_i,g_i}] \right\}.$$

(Formula 9)

This formula 9 is obtained through $\Psi_{Xi, \in i, gi}$ satisfying the variation principle, and further ensures the holding of the following inequality:

$$E_0 \le \min_i \left\{ \min_\Psi \bar{G}_{X_i,\varepsilon_i,g_i}[\Psi] + \Delta E_{X_i,\varepsilon_i,g_i}[\Psi_{X_i,\varepsilon_i,g_i}] \right\} \le$$
$$\min_i \left\{ \min_\Psi \bar{G}_{X_i,\varepsilon_i,g_i}[\Psi] + \Delta \bar{E}_{X_i,\varepsilon_i,g_i}[\Psi_{X_i,\varepsilon_i,g_i}] \right\}.$$

(Expression 10)

Figure 1:
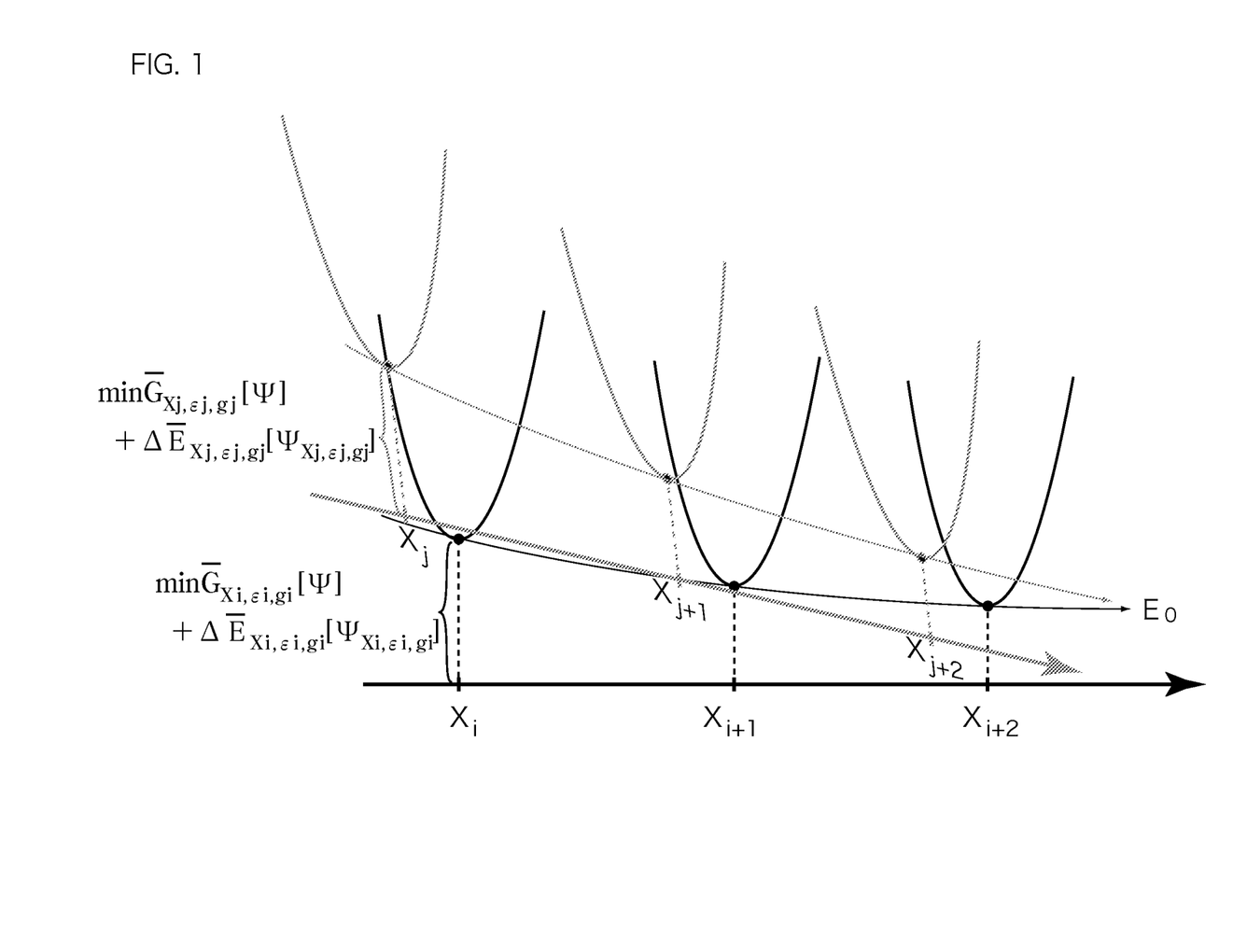
FIG. 1 is an explanatory view for explaining the calculation principle.

FIG. 1 is an explanatory view for explaining the calculation principle. According to the expression of formula 1, first, after the operation model is fixed, the energy functional $Gbar_{Xi, \in i, gi}$ is minimized, and then, the evaluated value of the variational energy is obtained, where the evaluated value is the sum of the minimized energy functional $Gbar_{Xi, \in i, gi}$ and $\Delta Ebar_{Xi, \in i, gi}$ determined by the wave function $\Psi_{Xi, \in i, gi}$ that provides the minimum value of $Gbar_{Xi, \in i, gi}$. Then, by executing the same calculation step with the operation model changed, a plurality of evaluation values of the variational energy are obtained. By using continuously changing the interaction parameters of a plurality of operation models in a space obtained by introducing a distance to a set containing the operation models as elements by using the absolute norm between electronic densities, an adjacent model series is obtained. As a result, an asymptotic curve that a variational energy change creates with respect to the interaction parameters can be obtained. By numerically evaluating the convergence value of this asymptotic curve, the evaluation value of the energy $E_0$ in the ground state is obtained. FIG. 1 shows that this method is present more than one in number. The operation model is constituted by $Gbar_{Xi, \in i, gi}$ and the wave function $\Psi_{Xi, \in i, gi}$ that provides the minimum value thereof. The wave function $\Psi_{Xi, \in i, gi}$ may be determined so as to have self-consistency with respect to a determination equation that determines the minimization problem of $Gbar_{Xi, \in i, gi}$ that forms a self-consistent equation.

As described later, a determination is performed as to the convergence properties of one model (for example, a model related to $X_i$ of FIG. 1) and another model (for example, a model related to $X_j$ of FIG. 1). At this time, it is determined whether or not a model sequence $X_i$ has converged with respect to the electron density and the variational energy in a model series $\{X_i\}$. It is also determined whether or not a model sequence $X_j$ in a model series $\{X_j\}$ has converged with respect to the electron density and the variational energy. In the present embodiment, physical quantity calculation is performed by using an effective model that model sequences including two kinds of operation models provide a common convergence point.

When the operation model is structured, the local density approximation method (LDA), the LDA+U, the generalized-gradient approximation method (GGA), spin-dependent GGA, meta-GGA, the Hartree-Fock method, the configuration interaction method, the perturbation MP (Moeller-Pleasset) method and those which are existing models that provide an approximation solution to the electronic state of a material may be used as the initial condition.

When the approximation solution provided by the calculation becomes sufficiently close to the neighborhood of the real solution (exact solution) by incorporating the contribution of necessary and sufficient fluctuations into $Gbar_{Xi, \in i, gi}$ by using the non-local operator expressed by formula 4, the differential with respect to a parameter change of the energy functional by the restricted search method becomes continuous from a universal energy functional $F_{\lambda=1}[\Psi]$ to the energy functional that determines $Gbar_{Xi, \in i, gi}$ (see formula 11), so that $n_\Psi(r)$ provided by the operation model is included in the same phase as the density provided by the Coulomb system. At this time, within the range of the determined numerical accuracy limit, the wave function $\Psi_{Xi, \in i, gi}$ provides the same physical properties as those shown by the exact solution.

$$F_{X_i}[\Psi] = \min_{\Psi' \to n_\Psi} \langle \Psi'|\hat{T} + \hat{V}^{X_i}_{red}|\Psi'\rangle.$$

(Formula 11)

Next, a method of confirming that the approximation solution provided by the operation model is sufficiently close to the neighborhood of the real solution (exact solution) will be disclosed. By providing a plurality of initial conditions and a plurality of orders to introduce fluctuations in combination, a plurality of operation model series asymptotic to the exact solution can be provided. At this time, an operation model series that generates a Cauchy sequence in the model space for each series can be always structured. Through the generation of quantization of one-electron orbitals clearly defined in each operation model, the procedure to generate a higher-ranked model series is defined. Accordingly, it is determined for each series that sufficient fluctuations are incorporated in all the series. That a plurality of series with respect evaluated by numerically confirming that the electron densities for models are approaching with each other. Therefore, when the approximation solution provided by all the numerically generated operation models generates a Cauchy sequence that provides the same limit with respect to the density, it is confirmed that it is sufficiently asymptotic to the neighborhood of the exact solution.

That is, in the present embodiment, since a plurality of paths that can attain the exact solution can be provided in a model space containing a wide variety of operation models, the path to incorporate the electron correlation can be set as appropriate. For example, by successively incorporating a strong correlation effect from the Fermi level and considering a correlation dependent on all the scales, the Coulomb interaction can be approached.

Therefore, by examining the numerical convergence with respect to the point sequence of the variational energy that appears when the parameter is changed like $X_i$, $X_{i+1}$, $X_{i+2}$ . . . , the direction asymptotic to the exact solution can be found.

That the properties in the ground state as the exact solution are reproduced is determined by the electron density coming not to change with respect to all the directions in which $X_i$ is changed. At this step, the electron density at the point of the procedure, when the minimization of the variational energy is completed, is obtained.

In order that a procedure to obtain an effective equation simplified by separating the degree of freedom from the expression of a field theory satisfying covariant invariance when a continuous coordinate space is set and a determination equation with respect to the steady state of a quantum-mechanical system is obtained as a differential equation on the continuous coordinate space, it is necessary that a degree of freedom that provides a variable quantity converted into a c number which quantity is provided by a physical quantity expectation value that is invariable in time be found out. An example thereof is, in an expression adopted as a Schroedinger equation of the electron system, a nuclear arrangement treated as a classical system of particles, and at the same time, is a static electric field treated as a classical field which is the solution of a Maxwell equation. By this problem setting, the generation of an order parameter which is the electron density and the determination of an effective Hamiltonian occur in association with the electron system. This always appears in a situation where an order parameter accompanied by spontaneous symmetry breaking in a real problem is generated. For the problem of determination of the quantum state of a pure many-particle system that cannot make known the generation of such a physical variable converted into a c number, the separation of the degree of freedom is indispensable. In the many-electron system where the real properties are discussed, from a result of an electron density measurement experiment, it has been determined that the separation of the degree of freedom is always possible in a condensed phase except when nuclear quantum fluidization at low temperature occurs.

If a degree of freedom that provides a certain variable quantity converted into a c number which quantity is provided by another physical quantity expectation value that is invariable in time is found when a determination equation with respect to the steady state of the quantum-mechanical system excluding this impossibility of the separation is obtained, it immediately becomes possible to improve the effective equation by using not only the density but a physical variable converted into a c number such as a more generalized order parameter. Therefore, according to the density functional variational method in the present application, a methodology that generally holds with respect to a many-body quantum system can be provided.

The generation of the density functional is due to the execution of the motion determination of the many-electron system in the external scalar potential. When the energy density functional is evaluated, if a conventional method including the conventional local density approximation, local spin density approximation, generalized-gradient approximation and spin-dependent generalized-gradient approximation where the function form is provided as a functional of general high versatility without depending on a physical system is used, it immediately becomes possible to apply the method disclosed in the present application.

An inventor of the present application provided, in WO 2007/141942, a fluctuation reference determination method as an effective many-body electronic calculation based on the multi-reference density functional method. By this determination method, in addition to the one-electron density, an energy functional that reproduces a variable (correlation function) having a positive definite property such as local density fluctuations is defined (see formula 12), and physical quantity reproduction can be performed.

$$G_{W_i}[\Psi] = \langle \Psi | \hat{T} + \hat{V}_{red}^{W_i} | \Psi \rangle + \tag{Formula 12}$$
$$\frac{e^2}{2} \int dr dr' \frac{n_\Psi(r) n_\Psi(r)}{|r-r'|} + E_{rxc}[n_\Psi] + \int dr n_\Psi(r) v_{ext}(r).$$

When the fluctuation reference determination method is used, by using a model having local density approximation to the residual exchange correlation energy functional of formula 12, an operation model can be immediately structured that is based on the density functional theory reproducing local fluctuations provided by an approximate electronic state calculation such as the Hartree-Fock method, the configuration interaction method and the perturbation MP method.

Therefore, by providing an operation model series by extending an operator space that determines the fluctuations to be incorporated by using, as the initial condition, an operation model that provides an approximate solution of the electronic state such as the Hartree-Fock method, the configuration interaction method and the perturbation MP, and finding a Cauchy sequence from the series, a procedure to attain the properties of the real solution can be provided. Further, by setting a numerical accuracy limit in this determination process, a calculation process that converges in finite calculation steps can be determined through the generation of a sequence of points $\{X_i\}$.

Figure 2:
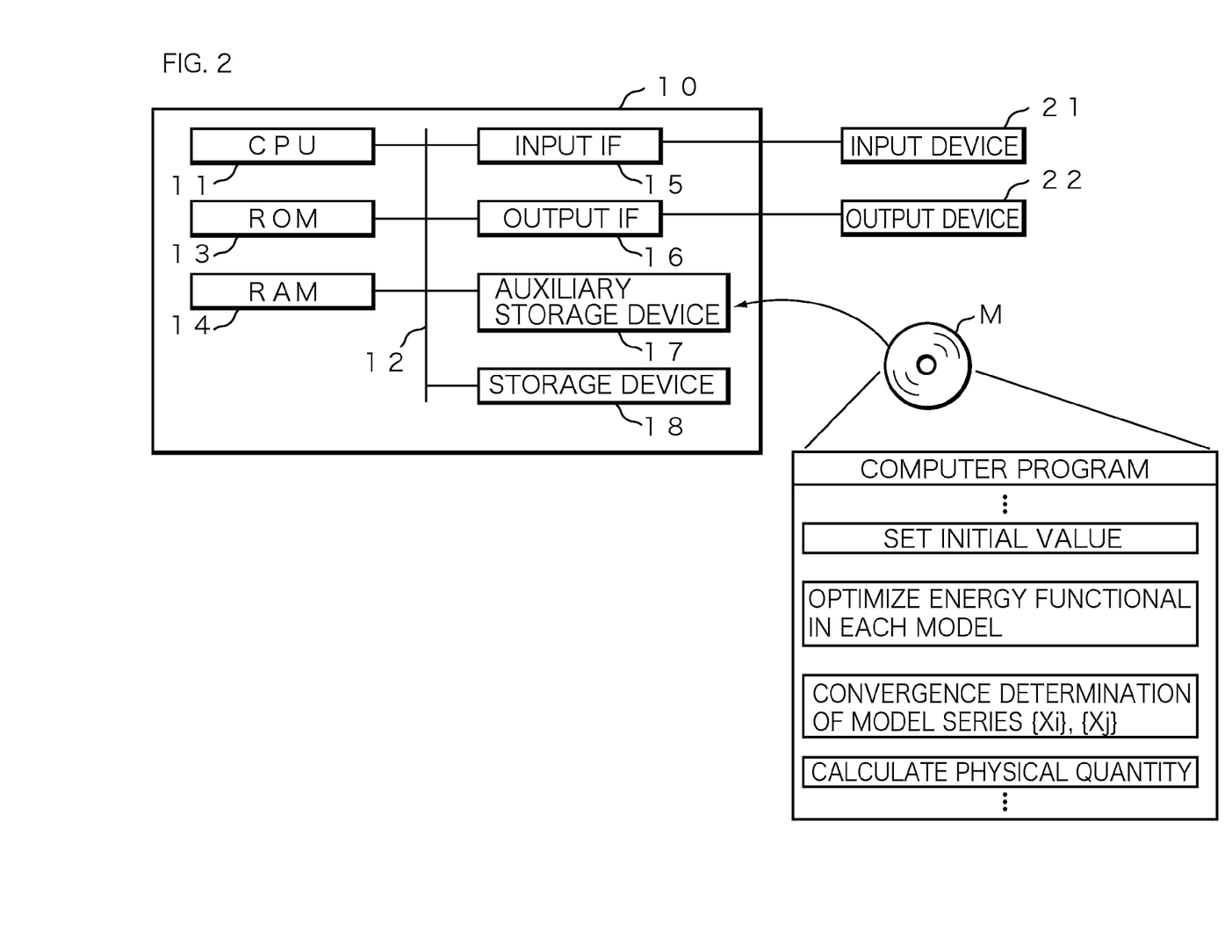
FIG. 2 is a block diagram showing the internal structure of an electronic state calculation device according to the present embodiment.

FIG. 2 is a block diagram showing the internal structure of an electronic state calculation device according to the present embodiment. The electronic state calculation device 10 is provided with a CPU 11, a ROM 13, a RAM 14, an input IF 15, an output IF 16, an auxiliary storage device 17 and a storage device 18, and these pieces of hardware are interconnected through a bus 12. The ROM 13 stores a control program for controlling the pieces of hardware. The CPU 11 controls the pieces of hardware by loading the control program stored in the ROM 13 onto the RAM 14 and executing it. To the input IF 15, an input device 21 such as a mouse and keyboard is connected. On the other hand, to the output IF 16, an output device 22 such as a CRT display or a liquid crystal display is connected.

The auxiliary storage device 17 is provided with a reading device such as an FD drive or a CD-ROM drive for reading a computer program for implementing the electronic state calculation method described in the present embodiment by a computer, from a recording medium M such as an FD or a CD-ROM recording the computer program. The computer program read by the auxiliary storage device 17 is stored in the storage device 18. The CPU 11 as operation means loads the computer program stored in the storage device 18 onto the RAM 14 as storage means and executes it, thereby causing the entire device to function as the electronic state calculation device according to the present application. The RAM 14 stores various pieces of information inputted through the input device 21, the interim result of the calculation by the CPU 11, the final result and the like in addition to the computer program.

As the recording device M recording the computer program, in addition to the above-mentioned FD and CD-ROM, the following may be used: an optical disk such as an MO, an MD or a DVD-ROM; a magnetic recording medium such as a hard disk; a card type recording medium such as an IC card, a memory card or an optical card; or a semiconductor memory such as a mask ROM, an EPROM (erasable programmable read only memory), an EEPROM (electrically erasable programmable read only memory) or a flash ROM. Moreover, the computer program may be downloaded through a communication network including the Internet by constructing a system to which the communication network is connectable. Further, the computer program may be prestored in the ROM 13.

The storage device 18 is, for example, a hard disk drive, and stores the computer program read by the auxiliary storage device 17, the initial data necessary for the electronic state calculation, the interim and final results obtained by the electronic state calculation, and the like. Part of the storage area of the storage device 18 is used as a model storage area for storing the existing models that provide an approximate solution to the electronic state of a material. This existing model includes, as mentioned above, the LDA, the LDA+U, the GGA, the spin-dependent GGA, the meta-GGA, the Hartree-Fock method, the configuration interaction method, and the perturbation MP method.

The computer program, the initial data, the operation models and the like stored in the storage device 18 are read when the electronic state is calculated, and temporarily stored in the ROM 13. The CPU 11 of the electronic state calculation device 10 performs the electronic state calculation by executing the computer program stored in the ROM 13.

While the computer program according to the present application recorded on the recording medium M is stored in the storage device 18 for use in the present embodiment, it may be previously incorporated in the ROM 13. Moreover, it is to be noted that the electronic state calculation device 10 may be provided with communication means so that the computer program is obtained through communication.

Figure 3:
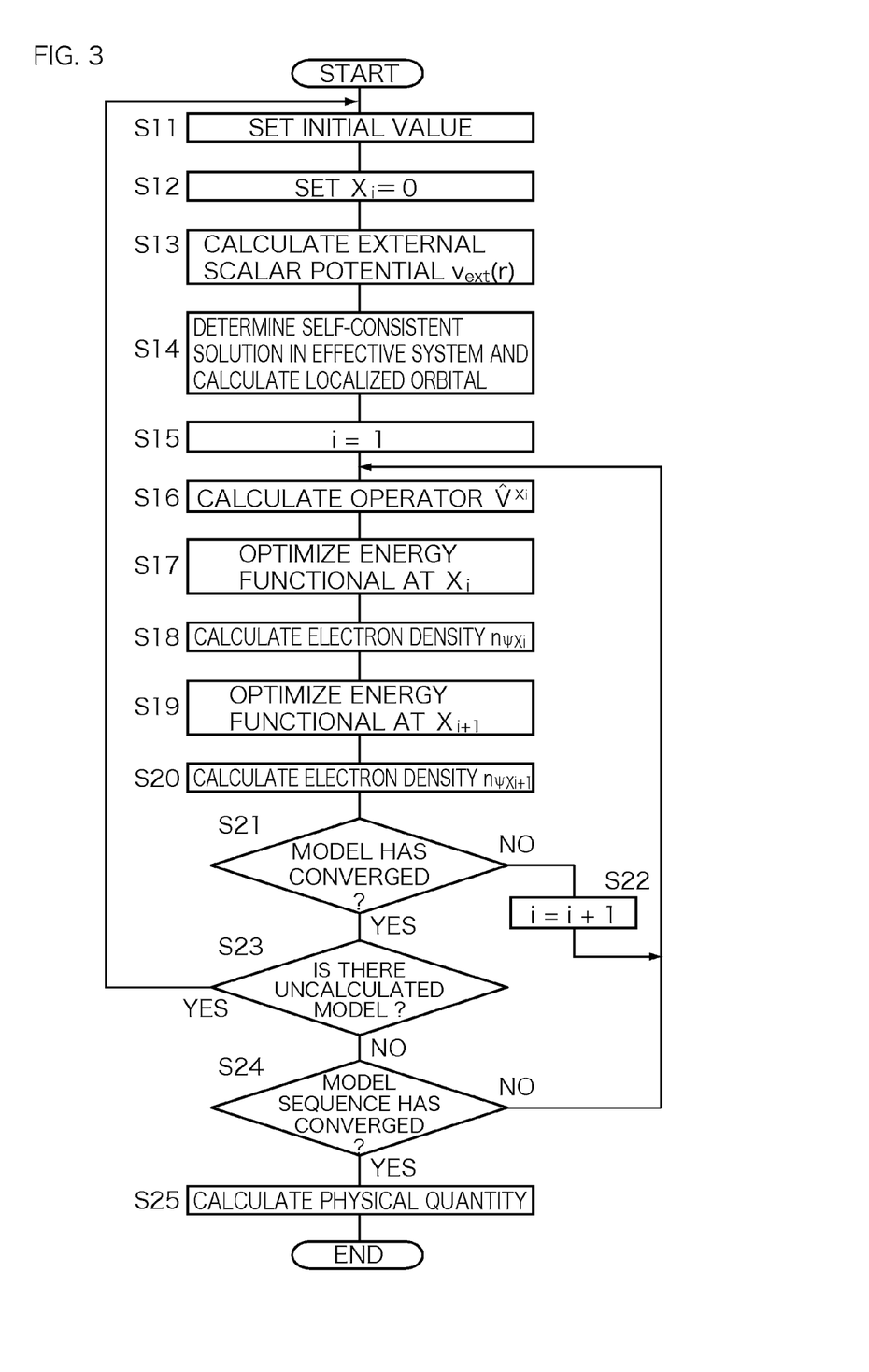
FIG. 3 is a flowchart showing the procedure of the processing executed by the electronic state calculation device.

Hereinafter, a concrete calculation procedure will be described. FIG. 3 is a flowchart showing the procedure of the processing executed by the electronic state calculation device 10. The electronic state calculation device 10 first performs initial value setting (step S11). The initial value setting is performed by setting the atomic coordinates $R_I$ of the material as the object of the calculation and determining $\in_i$ and $g_i$ to be combined with the form $X_i$ of the effective interaction. By performing the initial value setting, one model is determined. The setting of the atomic coordinates $R_I$ is performed by accepting the data of the atomic coordinates $R_I$ through the input device 21 and storing it in the RAM 14. Alternatively, the setting is performed by prestoring the data of the atomic coordinates $R_I$ in the storage device 18, reading the data from the storage device 18 when the setting is performed and storing it in the RAM 14.

Moreover, it is assumed that the function forms of $\in_1$ and $g_i$ and the like are provided as subroutines. $X_i$ represents a pair of fluctuation terms. The fluctuation terms are provided so as to include the interaction parameters $X_n^{(i)}$ and $\alpha_n^{(i)}$, for example, by formula 6.

Then, the electronic state calculation device 10 sets $X_i$ so that $X_i=0$ (i=1, 2, 3, ...) (step S12). Here, setting $X_i$ so that $X_i=0$ means setting the interaction parameter $X_n^{(i)}$ in formula 6 to zero.

Then, the CPU 11 of the electronic state calculation device 10 calculates the external scalar potential $v_{ext}(r)$ by using the set initial value (step S13). The method of calculation of the external scalar potential $v_{ext}(r)$ is known, and is uniquely determined from the atomic coordinates $R_I$.

Then, the CPU 11 of the electronic state calculation device 10 determines the effective system self-consistent solution, and calculates the localized orbital (step S14). The effective system self-consistent solution at $X_i=0$ is determined by a calculation routine such as the normal LDA. An integral expansion basis is provided as the initial value at this stage. A unitary conversion is determined according to the atomic coordinates $R_I$, and the localized orbital is calculated.

Then, after setting a loop counter i to 1 (step S15), the CPU 11 of the electronic state calculation device 10 calculates the operator $V_{red}^{Xi}$ (step S16). At this step, the forms and operations of the projection operator $P^{(i)}$ and the unitary conversion are provided as a series. That is, this means that the forms and operations of the projection operator and the unitary conversion may be updated by a loop. By the update, a higher-order model is attained.

Then, the CPU 11 of the electronic state calculation device 10 optimizes the energy functional at $X_i$ (step S17). When, in a model sequence which is a sequence of models having self-consistent solutions, the models provide the same density numerically in an error range and it is confirmed that the variational energy of the Coulomb system has a minimized value, it is determined that a converged model $X_i$ is obtained. The integral expansion basis is re-determined at this stage. Moreover, the unitary conversion is determined according to the atomic coordinates $R_I$, and the localized orbital is calculated.

Then, the CPU 11 of the electronic state calculation device 10 calculates the electron density $n_{\Psi Xi}$ (step S18). The electron density $n_{\Psi Xi}$ is calculated from the wave function $\Psi_{Xi}$ thereof with respect to the converged model.

Then, the CPU 11 of the electronic state calculation device 10 optimizes the energy functional at $X_{i+1}$ (step S19). In the present application, by changing the projection operator to $P^{(i+1)}$ and changing the unitary conversion at the same time, an up-conversion is performed to create a higher-order model $X_{i+1}$. In this higher-order model sequence, the converged model $X_{i+1}$ is obtained.

Then, the CPU 11 of the electronic state calculation device 10 calculates the electron density $n_{\Psi Xi+1}$ (step S20). The electron density $n_{\Psi Xi+1}$ is calculated from the wave function $\Psi_{Xi+1}$ thereof with respect to the converged model.

Then, the CPU 11 of the electronic state calculation device 10 determines whether the model has converged or not (step S21). The model series $\{X_i\}$ from the lower-order model $X_i$ to the higher-order model $X_{i+1}$ has already been provided. When the model sequence $X_i$ has converged with respect to the electron density and the variational energy in this model series $\{X_i\}$, it is determined that the model has converged.

When it is determined that the model series has not converged (S21: NO), the CPU 11 of the electronic state calculation device 10 increments the loop counter i by one (step S22), and returns the process to step S16.

When it is determined that the model has converged (S21: YES), the CPU 11 of the electronic state calculation device 10 determines whether there is an uncalculated model or not (step S23). When there is an uncalculated model (for example, the model related to $X_j$ shown in FIG. 1) (S23: YES), the process is returned to step S11, and the initial value is set for the uncalculated model. Then, by executing the processings at steps S12 to S21 on the newly set model, for example, the convergence property with respect to the model related to $X_j$ shown in FIG. 1 is determined.

When there is no uncalculated model (S23: NO), a plurality of model series $\{X_i\}$ and $\{X_j\}$ have already been obtained. The CPU 11 of the electronic state calculation device 10 determines whether a model sequence including these model series has converged or not (step S24). When these different model series obtain, with respect to the higher-order model to which they converge, a value to which the electron density provided thereby has converged, it is determined that the model sequence has converged.

When the model sequence has not converged (S24: NO), since fluctuations have not been sufficiently incorporated yet, update is performed for the projection operator and the unitary conversion that determine the higher-order model in the model series, and in order to perform the up-conversion of the model series again, the process is returned to step S16.

When it is determined that the model sequence has converged (S24: YES), physical quantity calculation is performed by using an effective model that the model sequence including the obtained two kinds of operation models provides as the common convergence point (step S25).

As described above, in the present embodiment, a plurality of model series starting from a plurality of integral effective models (LDA, GGA, etc.) to become asymptotic to the Coulomb solution can be structured.

The number of level intersections of the state shown by the energy functional method provided by the density functional method is finite. Moreover, since the integral effective Hamiltonian is always quantized, when the higher-order model is formed, the model series converges in a finite number of times. Therefore, the above model series attains the properties shown by the Coulomb solution by a finite number of times of calculation.

Moreover, in the present embodiment, since the fact is used that comparison between model series can be performed by using a distance related to the electron density, a method with the highest calculation efficiency among a plurality of model series can be determined by a finite number of times of calculation.

While the convergence property of the model sequence is determined by using two kinds of operation models in the present embodiment, the convergence property of the model sequence may be determined by using three or more kinds of operation models.

While the operation is executed while the operation model is successively updated with a specific operation model (for example, the local density approximation) as the starting point in the present embodiment, the self-consistent solution by each operation model may be obtained by a parallel calculation using the LAPW method (linearized augmented plane wave method) and the numerical basis expansion method.

Second Embodiment

An up-conversion process may be introduced to the electronic state calculation method described in the first embodiment.

In the second embodiment, a form will be described in which the up-conversion process is introduced to the electronic state calculation method of the first embodiment.

The following formula 13 is a definitional equation of a model used for the second embodiment of the up-conversion method, by a model in which the projection operator is introduced to one-electron bands or one-electron orbitals for which the fluctuation effect is important, and a screened interaction type interaction strength is introduced as a parameter to adjust the strength of the effective interaction provided by the fluctuation term.

$$\bar{G}_{\lambda,A}[\Psi] = \langle\Psi|\hat{T} + \hat{V}(\lambda)|\Psi\rangle + \frac{e^2}{2}\int drdr' \frac{n_\Psi(r)n_\Psi(r)}{|r-r'|} + \quad \text{(Formula 13)}$$

$$(1-\lambda)E_{rxc}[n_\Psi] + \int dr n_\Psi(r)v_{ext}(r),$$

$$\hat{V}(\lambda) = \lambda\left\{\frac{1}{2}\int d^3rd^3r'\frac{e^2}{|r-r'|}:\right.$$

$$\hat{n}(r)\hat{n}(r'): -\frac{1}{2}\int d^3rd^3r'\frac{e^2}{|r-r'|}n_\Psi(r)n_\Psi(r') -$$

$$\frac{1}{2}\int d^3rd^3r'\frac{e^2e^{-\kappa(1-\lambda)|r-r'|}}{|r-r'|}[\hat{P}_A:\hat{n}(r)\hat{n}(r'):\hat{P}_A -$$

$$\langle\Psi|\hat{P}_A\hat{n}(r)\hat{P}_A|\Psi\rangle\langle\Psi|\hat{P}_A\hat{n}(r')\hat{P}_A|\Psi\rangle] +$$

$$\frac{1}{2}\int d^3rd^3r'\frac{e^2e^{-\kappa(1-\lambda)|r-r'|}}{|r-r'|}[\hat{P}_A:\hat{n}(r)\hat{n}(r'):\hat{P}_A -$$

$$\langle\Psi|\hat{P}_A\hat{n}(r)\hat{P}_A|\Psi\rangle\langle\Psi|\hat{P}_A\hat{n}(r')\hat{P}_A|\Psi\rangle].$$

The up-conversion process may be summed up as a two-stage process when the initial model is taken in the LDA or the like. First, the one-electron band and the one-electron orbital to which fluctuations are introduced are successively incorporated from the neighborhood of the Fermi level.

Here, if a parameter $\kappa$ that determines the screened interaction is introduced to a positive finite value, an intermediate range correlation effect is incorporated first.

As described in the first embodiment, when a model showing the convergence point of a model sequence is obtained, since a Bloch orbital or a Wannier orbital that characterizes this model is obtained, a projection operator $P_A$ hat determined by these orbitals is introduced. Here, $\lambda$ is a parameter indicating the second process of the up-conversion method by a single continuous parameter from above-mentioned models taking quantum fluctuations in, to the final Coulomb system, and takes numerical values from 0 to 1.

As a concrete embodiment, an electronic state calculation of $Sr_2$ and $CuO_3$ will be taken as an example.

By checking the solution of the Kohn-Sham equation by the GGA, it can be immediately confirmed that one one-dimensional band per Cu atom is generated in the neighborhood of the Fermi level. The projection operator is introduced to the Wannier orbital on this band. Incorporating the screened interaction corresponds to starting the first process of the up-conversion from only a diagonal interaction term on the Wannier orbital. Therefore, as the correlation parameter, U provided by the integral of the screened interaction is adopted as the single parameter. The multi-reference density functional method calculation to which the interaction parameter is introduced is capable of providing a solution to the self-consistency. By changing this parameter U, the many-electron state by the multi-reference density functional method is provided along with a density while a state vector where a quantum correlation is caused is the self-consistent solution. By evaluating ΔEbar according to the variation principle of the density functional variational method, the variational energy is obtained as a function of U.

Figure 4:
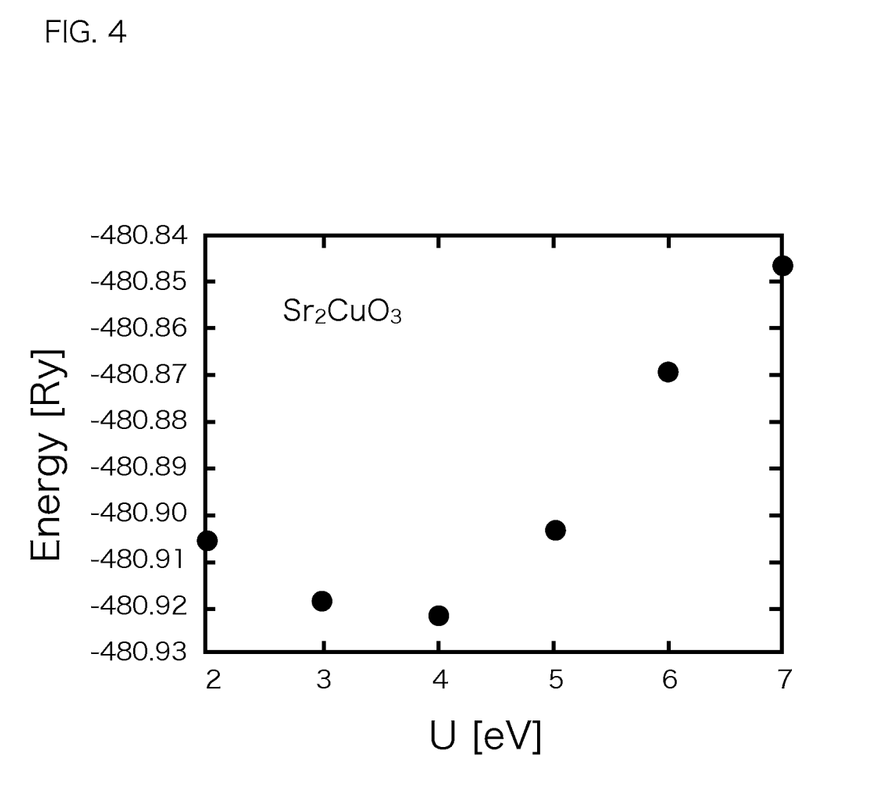
FIG. 4 is a view showing an example of the result of the variational energy evaluation.

FIG. 4 is a view showing an example of the result of the variational energy evaluation. In FIG. 4, the horizontal axis represents the correlation parameter U (the unit is electron volt), and the vertical line represents the variational energy (the unit is rydberg). Here, it has been found that the variational energy provided by the model is a continuous function of the correlation parameter U. As is apparent from this view, by the density functional variational method, the optimized correlation parameter to minimize the variational energy can be determined.

The second process of the up-conversion can also be executed by further using the model of the determined correlation parameter as the initial condition. In that case, the process can be performed by verifying the presence or absence of the occurrence of a phase transition in the model space by causing the model series to change by incorporating the residual correlation while changing λ, and numerically tracking the change.

Here, the evaluation of the energy provided by the model series when λ is changed can be performed by the perturbational expansion Green's function method, the Monte Carlo method or the like. According to the perturbational expansion Green's function method, a Green's function $G_0$ including the local correlation effect determined when the correlation parameter U is finite is obtained, and based on it, a long range interaction effect can be performed through the analysis of a Dyson equation.

As the approximate evaluation method in this case, by using $G_0$ as the input Green's function in the GW approximation, the convergence of the up-conversion process is confirmed through the density not being changed by a one-shot calculation because of the incorporation of a screening effect. When a density change appears, the first process of the up-conversion is performed again by performing further addition of a correlation term through the redefinition of the projection operator $\hat{P}_A$ and performing the multi-reference density functional method calculation again.

According to the Monte Carlo method, a calculation incorporating an extremely short range correlation effect can be performed by obtaining a state vector including the local correlation effect determined when the correlation parameter U is finite and adopting a many-body wave function based on it as the trial function for the node fixing of a diffusion Monte Carlo method. As the approximate evaluation method in this case, a fixed-node approximation diffusion Monte Carlo method, a variational Monte Carlo method or the like may be adopted.

Third Embodiment

By using the electronic state calculation method described in the first and second embodiments, an optimized operation model where the number of times of calculation is the smallest while the physical properties shown by the exact solution are reproduced can be determined.

In the third embodiment, a method of selection of the optimized operation model will be described.

Formula 14 shown below shows a model functional that provides a continuous model series that connects with the Coulomb system by the single continuous parameter with convexity. Vhat/tilde(λ) is provided as a correlation term that generates a positive definite operator from the λ differential. The value of λ takes a value from 0 to 1, and at λ=1, the original Coulomb interaction system is reproduced.

$$\overline{G}_{\lambda,A}[\Psi] = \langle \Psi | \hat{T} + \tilde{V}(\lambda) | \Psi \rangle + \frac{e^2}{2} \int dr dr' \frac{n_\Psi(r) n_\Psi(r)}{|r-r'|} + \quad \text{(Formula 14)}$$

$$(1-\lambda) E_{rxc}[n_\Psi] + \int dr n_\Psi(r) v_{ext}(r),$$

$$\tilde{V}(\lambda) = \lambda \left\{ \frac{1}{2} \int d^3r d^3r' \frac{e^2}{|r-r'|} : \right.$$

$$\hat{n}(r)\hat{n}(r') : -\frac{1}{2} \int d^3r d^3r' \frac{e^2}{|r-r'|} n_\Psi(r) n_\Psi(r') -$$

$$\frac{1}{2} \int d^3r d^3r' \frac{e^2 e^{-\kappa(1-\lambda)|r-r'|}}{|r-r'|}$$

$$\left[ : \hat{n}(r)\hat{n}(r') : -\langle \Psi | \hat{n}(r) | \Psi \rangle \langle \Psi | \hat{n}(r') | \Psi \rangle | \right] +$$

$$\frac{1}{2} \int d^3r d^3r' \frac{e^2 e^{-\kappa(1-\lambda)|r-r'|}}{|r-r'|}$$

$$\left[ : \tilde{\hat{n}}(r)\tilde{\hat{n}}(r') : -\langle \Psi | \tilde{\hat{n}}(r) | \Psi \rangle \langle \Psi | \tilde{\hat{n}}(r') | \Psi \rangle \right],$$

$$\tilde{\hat{n}}(r) \equiv \hat{P}_A \hat{n}(r) + \hat{n}(r) \hat{P}_A - \hat{P}_A \hat{n}(r) \hat{P}_A,$$

$$: \tilde{\hat{n}}(r)\hat{n}(r') : \equiv \hat{P}_A : \hat{n}(r)\hat{n}(r') : + : \hat{n}(r)\hat{n}(r') :$$

$$\hat{P}_A - \hat{P}_A : \hat{n}(r)\hat{n}(r') : \hat{P}_A.$$

At λ=0, for the correlation term, a model interaction term defined by using the projection operator set to ensure convexity is included. This term can be constructed based on the solution at λ=0 of formula 13.

The optimized solution of the model at λ=0 of formula 14 is one the energy of which can be evaluated by the perturbational expansion using Green's function method. This is the first process of the up-conversion using the redefinition of the projection operator $P_A$. At this time, a case, where the energy evaluation is possible without the density changed, can be searched for.

Then, the effect by changing λ from 0 to 1 is evaluated by a variational calculation. In the second process of the up-conversion provided by formula 14, the λ differential of the model functional provided by the operator with a tilde of nhat/tilde(r) is a positive definite and a condition for the finiteness theorem of the number of times of phase transition to hold is provided accordingly. This condition is the invariability of the density in the up-conversion process.

Therefore, by the confirmation of the density invariability in the second process where calculation execution is possible, it is confirmed that a further up-conversion process is unnecessary, and the determination of convergence of all the processes is possible in an error range determined in a finite numerical calculation process.

Figure 5:
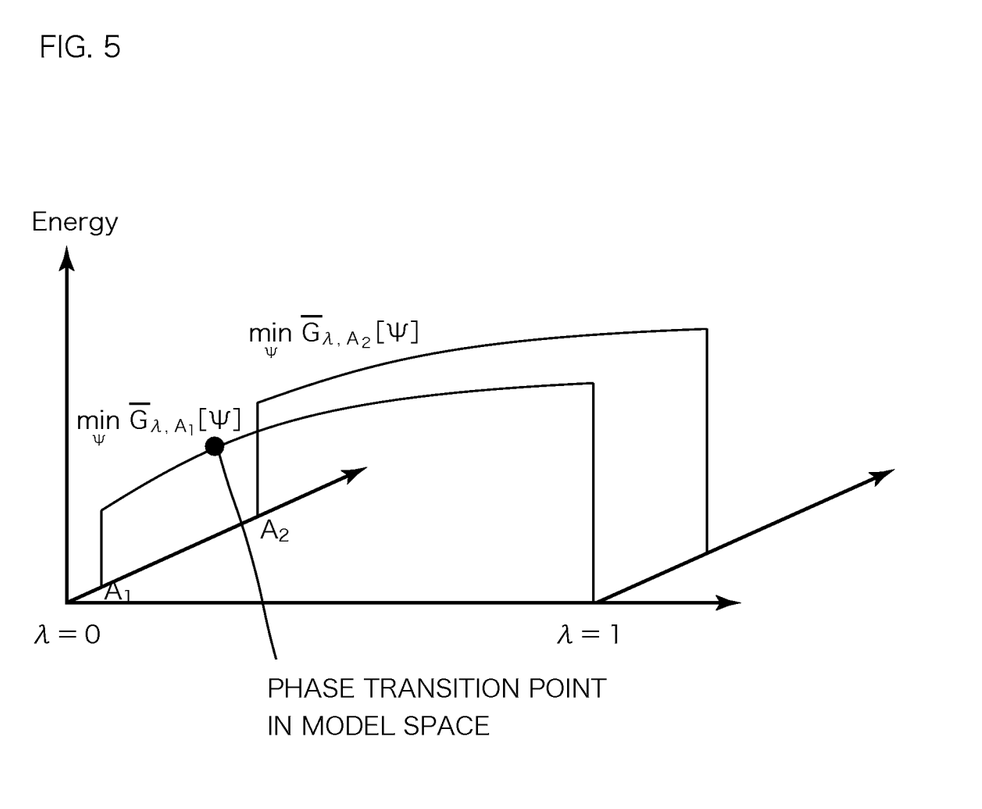
FIG. 5 is an explanatory view for explaining the principle that provides the optimized model determination process.

FIG. 5 is an explanatory view for explaining the principle that provides the optimized model determination process. It is assumed that a plurality of convergence model sequences have already been provided through the first embodiment. In this condition, a λ-converted model can be structured according to formula 14. In this λ conversion process, convergence with respect to the density has already been sufficiently obtained. Keeping the density unchanged, the number of times of occurrence of phase transition point due to remaining correlation is a finite number at the most. Although not clearly shown in FIG. 5, the phase transition point occurs as the inflection point of the graph that appears with respect to the change of the parameter λ, and at this point, the λ Dini derivative shows a jump. In this process, it is used that, in the models reproducing the physical properties shown by the exact solution, the phase transition in the model space due to a change of an internal order parameter does not happen.

By selecting a model in which the converged density is reproduced and λ=0 can be attained starting from the convergence point of the model incorporating a sufficient correlation without the occurrence of a phase transition point, an optimized model where the number of times of calculation is the smallest, while the properties shown by the exact solution are reproduced, can be selected.

Figure 6:
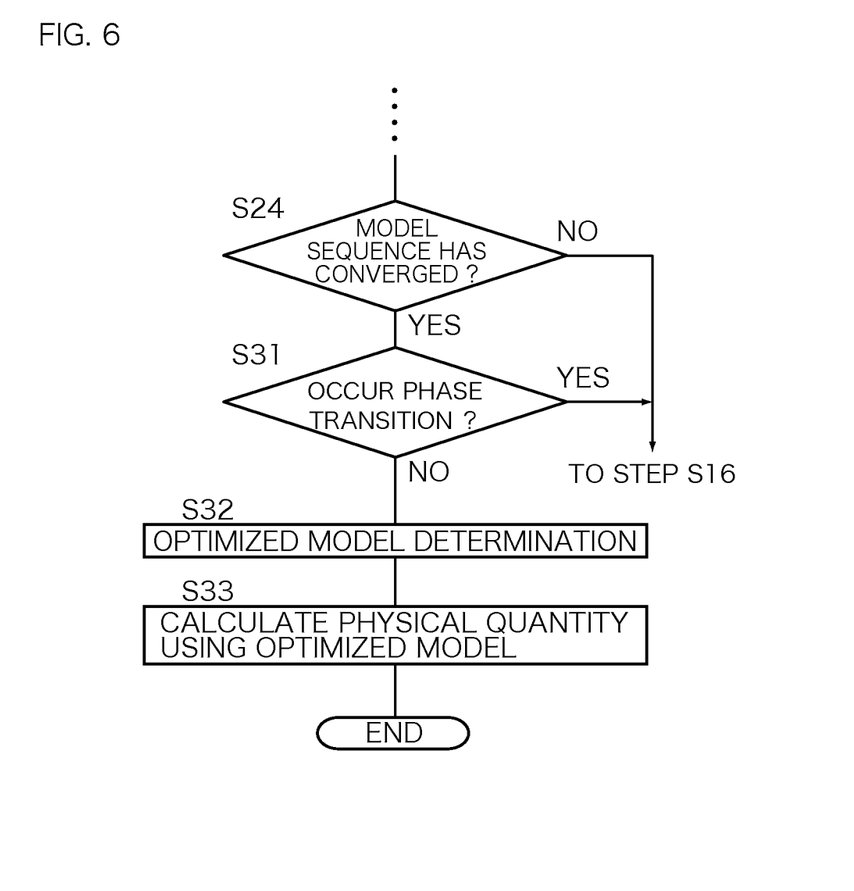
FIG. 6 is a flowchart showing the procedure of the processing that the electronic state calculation device executes to determine the optimized model.

While confirmation through a phase transition occurrence can be performed from the principle of FIG. 5, a method for implementing this by a numerical calculation is a flowchart, shown in FIG. 6, showing the procedure of the processing that the electronic state calculation device executes for optimized model determination. It is assumed that a plurality of converged model sequences are obtained by step S11 to step S24 of the flowchart shown in FIG. 3 of the first embodiment. Then, by checking the phase difference at λ=0 among a plurality of models that provide the converged density, the electronic state calculation device determines whether or not a phase transition has occurred due to a change of the internal order parameter although it is determined that the density is converged (step S31). When it is confirmed that there is a phase transition occurrence at the λ conversion, for example, when the two model series of FIG. 5 are obtained (S31: YES), the model sequences thereof are rejected, and the process returns to S16 to search for a model series further incorporating fluctuations until it is confirmed that the converged model series provide the same phase. When it is confirmed that there is no phase transition occurrence at step S31 (S31: NO), a model sequence including a plurality of model series that provide the same phase are obtained. At this time, the phase transition occurrence with respect to the λ conversion is confirmed by there being no change of various responses in addition to there being no density change in the second process of the up-conversion by the perturbational expansion Green's function method on the algorithm.

At this step, a plurality of model series showing the same properties on a higher order of the λ conversion provides confirmation of having obtained the real solution of the system. When this condition is satisfied, the optimized model determination is performed by selecting one with no phase transition occurrence up to a low-order model of the λ conversion process (step S32).

Lastly, the physical quantity calculation using the optimized model is performed (step S33), so that a property evaluation by a model system most appropriately selected for the calculation scale becomes possible.

While in the above-described embodiments, the electronic state optimization calculation with respect to a known crystal structure has been described, the dynamics of a system may be calculated by using a technique of molecular dynamics. To calculate the dynamics of a system, the effective many-body wave function at a certain time evolution step is obtained, and an MD (molecular dynamics) calculation is performed for the bulk order. For this MD calculation, the following technique is adopted: First, by using the electron density, the external scalar potential and the localized orbital obtained by the extended Kohn-Sham equation, the atomic force and the stress are obtained, the material structure change rate is calculated from the obtained atomic force and stress, and the material structure after a short time period is successively determined.

Moreover, the highly accurately determined ground state obtained in the present embodiments or a mode of a molecular dynamics method can be continuously used as the initial condition for the time-dependent problem. By this method, a time-dependent current density functional method using the electron density and the current density as basic order parameter can be realized.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A method of calculating an electronic state of a material by using a calculation device, the method comprising:

setting a set containing, as elements, a plurality of operation models loaded in a memory of the calculation device by using the calculation device, where each of the operation models provides an approximate solution to an exact solution of the electronic state of the material;

determining, in order to specify all of the operation models, for each operation model, an effective Hamiltonian including effective interactions that act on an electron system containing two or more electrons existing on a plurality of electron orbitals, by using the calculation device;

determining, in a process of calculating a self-consistent solution of the effective Hamiltonian by using each of the operation models in the set, an optimized operation model among a plurality of operation models that are close in distance in a space obtained by introducing a distance to the set through a use of an absolute norm between electronic densities given by the operation models, based on a quantum mechanical variational method while defining a direction in which the calculated self-consistent solutions continuously change by using the calculation device;

evaluating, when the optimized operation model is successively updated, a variational energy of the electron system by the self-consistent solution of the effective Hamiltonian by using the calculation device;

updating the optimized operation model by using the calculation device so that the evaluated variational energy approaches an energy of the exact solution to be calculated and further, so that the variational energy forms a monotonically decreasing convex function;

calculating the exact solution of the electronic state from one or a plurality of variational energy series by using the calculation device, and executing an operation of storing the calculated exact solution or a series of the variational energy that approaches the exact solution in the memory by using the calculation device;

wherein among one or a plurality of series of the operation models that provide a series of the variational energy that approaches the exact solution, the series that includes the following operation model is determined by the calculation device, wherein the operation model provides a quantum phase shown by the electronic state, the quantum phase is equated with the exact solution without occurring a phase transition, and the operation model attains the self-consistent solution of the effective Hamiltonian by a minimum number of calculation steps, and wherein all of the operation models which are contained in the set are defined to be those satisfying following conditions (i) to (v), (i) the operation models obey a variational principle of a quantum mechanics, (ii) the series of the operation models is a coverging series with respect to a primary order parameter of the electron system, where the primary order parameter is electron density, (iii) the series has no phase transition point among the operation models in the series, (iv) each of the operation models has a continuous modification path connecting to an exact quantum mechanical representation of the material, (v) without the phase transition point, each of the operation models connects to a higher-ranked model series where a lambda-modification path defined by subtraction of a positive-definite functional from the exact quantum mechanical representation exists.

2. The electronic state calculation method according to claim 1, wherein the effective Hamiltonian is determined through a procedure of determining non-local operators indicating fluctuations as the effective interactions, based on a local density approximation method, a generalized-gradient approximation method or a Hartree-Fock method.

3. The electronic state calculation method according to claim 2, wherein the fluctuations include density fluctuations which are equal to the deviation of a Hartree mean-field term and a Coulomb interaction.

4. The electronic state calculation method according to claim 1, wherein the self-consistent solution by each of the operation models is obtained by a parallel calculation using an LAPW (linearized augmented plane wave) method, a PAW (projector augmented wave) method or a numerical basis expansion method.

5. A device that calculates an electronic state of a material comprising:

a setting part configured to set a set containing, as elements, a plurality of operation models loaded in a memory of the device, where each of the operation models provides an approximate solution to an exact solution of the electronic state of the material;

a first determining part configured to determine, in order to specify all of the operation models, for each operation model, an effective Hamiltonian including effective interactions that act on an electron system containing two or more electrons existing on a plurality of electron orbitals;

a second determining part configured to determine, in a process of calculating a self-consistent solution of the effective Hamiltonian by using each of the operation models in the set, an optimized operation model among a plurality of operation models that are close in distance in a space obtained by introducing a distance to the set through a use of an absolute norm between electronic densities given by the operation models, based on a quantum mechanical variational method while defining a direction in which the calculated self-consistent solutions continuously change;

an evaluating part configured to evaluate, when the optimized operation model is successively updated, a variational energy of the electron system by the self-consistent solution of the effective Hamiltonian;

an updating part configured to update the optimized operation model so that the evaluated variational energy approaches an energy of the exact solution to be calculated and further, so that the variational energy forms a monotonically decreasing convex function;

a calculating part configured to calculate the exact solution of the electronic state from one or a plurality of variational energy series, and a storing part configured to store the calculated exact solution or a series of the variational energy that approaches the exact solution in the memory;

wherein among one or a plurality of series of the operation models that provide a series of the variational energy that approaches the exact solution, the series that includes the following operation model is determined by the device, wherein the operation model provides a quantum phase shown by the electronic state, the quantum phase is equated with the exact solution without occurring a phase transition, and the operation model attains the self-consistent solution of the effective Hamiltonian by a minimum number of calculation steps, and wherein all of the operation models which are contained in the set are defined to be those satisfying following conditions (i) to (v), (i) the operation models obey a variational principle of a quantum mechanics, (ii) the series of the operation models is a coverging series with respect to a primary order parameter of the electron system, where the primary order parameter is electron density, (iii) the series has no phase transition point among the operation models in the series, (iv) each of the operation models has a continuous modification path connecting to an exact quantum mechanical representation of the material, (v) without the phase transition point, each of the operation models connects to a higher-ranked model series where a lambda-modification path defined by subtraction of a positive-definite functional from the exact quantum mechanical representation exists.

6. The electronic state calculation device according to claim 5, wherein the effective Hamiltonian is determined through a procedure of determining non-local operators indicating fluctuations as the effective interactions, based on a local density approximation method, a generalized-gradient approximation method or a Hartree-Fock method.

7. The electronic state calculation device according to claim 6, wherein the fluctuations include density fluctuations which are equal to the deviation of a Hartree mean-field term and a Coulomb interaction.

8. The electronic state calculation device according to claim 5, wherein the self-consistent solution by each of the operation models is obtained by a parallel calculation using an LAPW (linearized augmented plane wave) method, a PAW (projector augmented wave) method or a numerical basis expansion method.

9. A non-transitory computer readable recording medium storing a computer program for causing a computer to calculate an electronic state of a material, the computer program comprising the steps of:

causing the computer to set a set containing, as elements, a plurality of operation models loaded in a memory of the computer, where each of the operation models provides an approximate solution to an exact solution of the electronic state of the material;

causing the computer to determine, in order to specify all of the operation models, for each operation model, an effective Hamiltonian including effective interactions that act on an electron system containing two or more electrons existing on a plurality of electron orbitals;

causing the computer to determine, in a process of calculating a self-consistent solution of the effective Hamiltonian by using each of the operation models in the set, an optimized operation model among a plurality of operation models that are close in distance in a space obtained by introducing a distance to the set through a use of an absolute norm between electronic densities given by the operation models, based on a quantum mechanical variational method while defining a direction in which the calculated self-consistent solutions continuously change;

causing the computer to evaluate, when the optimized operation model is successively updated, a variational energy of the electron system by the self-consistent solution of the effective Hamiltonian;

causing the computer to update the optimized operation model so that the evaluated variational energy approaches an energy of the exact solution to be calculated and further, so that the variational energy forms a monotonically decreasing convex function;

causing the computer to calculate the exact solution of the electronic state from one or a plurality of variational energy series, and causing the computer to execute an operation of storing the calculated exact solution or a series of the variational energy that approaches the exact solution in the memory;

wherein among one or a plurality of series of the operation models that provide a series of the variational energy that approaches the exact solution, the series that includes the following operation model is determined by the computer, wherein the operation model provides a quantum phase shown by the electronic state, the quantum phase is equated with the exact solution without occurring a phase transition, and the operation model attains the self-consistent solution of the effective Hamiltonian by a minimum number of calculation steps, and wherein all of the operation models which are contained in the set are defined to be those satisfying following conditions (i) to (v), (i) the operation models obey a variational principle of a quantum mechanics, (ii) the series of the operation models is a coverging series with respect to a primary order parameter of the electron system, where the primary order parameter is electron density, (iii) the series has no phase transition point among the operation models in the series, (iv) each of the operation models has a continuous modification path connecting to an exact quantum mechanical representation of the material, (v) without the phase transition point, each of the operation models connects to a higher-ranked model series where a lambda-modification path defined by subtraction of a positive-definite functional from the exact quantum mechanical representation exists.

* * * * *